United States Patent [19]

Spira et al.

[11] Patent Number: 5,607,845
[45] Date of Patent: Mar. 4, 1997

[54] METHOD FOR OBTAINING AN INCREASED PRODUCTION OF A PRODUCING CELL LINE BY USING A FUSION PROTOCOL

[75] Inventors: Jack Spira, Solna; Lars Adamsson, Lidingö, both of Sweden

[73] Assignee: Pharmacia & Upjohn AB, Stockholm, Sweden

[21] Appl. No.: 505,189

[22] PCT Filed: Feb. 15, 1994

[86] PCT No.: PCT/SE94/00123

§ 371 Date: Aug. 14, 1995

§ 102(e) Date: Aug. 14, 1995

[87] PCT Pub. No.: WO94/19459

PCT Pub. Date: Sep. 1, 1994

[30] Foreign Application Priority Data

Feb. 16, 1993 [SE] Sweden ................... 9300509

[51] Int. Cl.⁶ .......................... C12P 21/00; C12N 15/02; C12N 15/06; C12N 15/67
[52] U.S. Cl. .................. 435/69.1; 435/70.2; 435/172.2; 435/173.8; 935/34; 935/89; 935/93; 935/95; 935/106; 935/109
[58] Field of Search .................. 435/69.1, 41, 70.1, 435/70.2, 70.3, 172.2, 173.1, 173.8, 240.2, 240.26; 935/33, 34, 89, 90, 93, 95, 102, 106, 109

[56] References Cited

U.S. PATENT DOCUMENTS 4,659,663  4/1987  Wright ................... 435/172.2
4,822,470  4/1989  Chang ................... 435/172.2
4,832,814  5/1989  Root ...................... 435/207
4,959,321  9/1990  Preece et al. ........... 204/604

FOREIGN PATENT DOCUMENTS

WO91/09122  6/1991  WIPO.
WO92/16557  10/1992  WIPO.

OTHER PUBLICATIONS

Hotta et al. "New Antibiotic-Producing Steptomyces, Selected By Antibiotic Resistance As a Marker" J. Antibiot. 38(1) 64–69 1985.

Chenciner et al. "Enhancement of Gene Expression By Somatic Hybridization w/Primary Cells" Bio/Technology 8 858–862 1990.

Roos et al. "Control of Virus-Induced Cell Fusion by Host Cell Lipid Composition" Virology 175 345–357 1990.

*Primary Examiner*—Mindy Fleisher
*Assistant Examiner*—Nancy J. Degen
*Attorney, Agent, or Firm*—Pollock, Vande Sande & Priddy

[57] ABSTRACT

The invention relates to a method for obtaining a higher product expression in a producing mammalian cell line characterized by treating the original cell line with itself according to a fusion protocol known in the art. The production of protein products is performed in mammalian tissue culture, and the product could be therapeutic proteins or other molecules intended for human use. In particular, this invention relates to the use of cell fusion methods to obtain a stable high producing cell line.

21 Claims, No Drawings

METHOD FOR OBTAINING AN INCREASED PRODUCTION OF A PRODUCING CELL LINE BY USING A FUSION PROTOCOL

FIELD OF INVENTION

The present invention relates to a method for obtaining a higher product expression in a producing mammalian cell line characterized by treating the original cell line with itself according to a fusion protocol, known in the art. The production of protein products is performed in mammalian tissue culture, and the product could be therapeutic proteins or other molecules intended for human use. In particular this invention relates to the use of cell fusion methods to obtain a stable high producing cell line.

DESCRIPTION OF THE RELATED ART

Expression of proteins in heterologous mammalian cells is usually performed in one of the following three ways, well known to the artisan in the field.

1) A vector or virus containing necessary elements for expression of proteins in mammalian cells may be introduced in an appropriate cell.
2) A primary cell line expressing a certain protein may be transformed to a continuous cell line.
3) A primary cell line, such as a lymphocyte may be fused to a nonproducing cell line and the resulting hybrid can be selected for expression of the wanted protein.

By further cultivation of cells derived from 1–3 above the protein of interest can be obtained from the culture medium or the cells themselves.

The latter technique 3 is the most common one and is used for production of monoclonal antibodies by hybridoma cells. Hybrid cell lines are usually characterized by presence of chromosomes or genes from the two different fusion parents and require some sort of selection procedure in order to eliminate the parental cells from the fusion mixture and allowing the emergence and outgrowth of the fused cell.

Cell fusion as a method of enhancing protein production has been described by Chenciner et al in Bio/Technology vol 8, 1990:858–862. The authors produced classical hybrids between a liver cell and a transfected Vero cell. The stable hybrids produced an increased amount of the wanted product.

Different cell fusion protocols are well known in the art. The use of polyethylene glycol (PEG), protoplasts or Sendaivirus can be mentioned as examples and reference is here given to Cell culture by William B. Jakoby and Ira H. Pastan, Methods in Enzymology Vol. LVIII, Academic Press, 1979. Electrofusion is another method that also can be used and reference is here given to Electromanipulation in hybridoma technology, Laboratory manual, by Carl A. K. Borrbaeck and Inger Hagen, Stockman Press, 1989 and Guide to Electroporation and Electrofusion, Chang et al, Academic Press, 1992. By variations of e.g. the used amount of cells, time, temperature etc., each laboratory often has its own protocol.

In summary the above described prior art discloses the use of classical cell fusion of two different cells, as means of obtaining and increasing production of a particular product in a particular cell which is a fusion cell, a combination of the two parent cells.

We have now found a method that can be used in the establishment of a protein producing cell line. The method will increase the production of the wanted product of the cell line.

Although the method resembles cell fusion it is not a classical cell fusion and the cell lines obtained are, to our great surprise, stable over a prolonged period.

SUMMARY OF THE INVENTION

The present invention relates to a method of obtaining a higher product expression in a producing cell line by fusing the original cell with itself according to a fusion protocol, known in the art.

Cell fusion protocols suitable for the present invention are methods utilizing polyethylene glycol (PEG) or electrofusion, protoplasts or Sendaivirus. The cell could be a Chinese Hamster Ovary (CHO) derived cell line, Baby Hamster Kidney (BHK) or Cos (an African green monkey derived cell line) or any other commonly used mammalian cell line.

The product is preferably full length factor VIII, deletion derivatives of factor VIII or otherwise modified factor VIII but could also be another therapeutically active protein or molecule.

The resulting cell lines could have a chromosome and DNA content identical or very similar to the original cell line.

The cell fusion protocol is preferably performed without the presence of a selection protocol, but selection protocols could be used.

The fusion protocol could be performed on already fused cells.

The invention also relates to the use of a cell line or cell which has been obtained by fusing the original cell with itself according to fusion protocol in the production of a protein or another molecule and preferably a cell line in which the cell lines have a chromosome and DNA content similar the original cell line.

The present invention comprises thus the use of a cell fusion protocol to increase the productivity of a mammalian cell line.

A preferred aspect of the present invention is the use of the method to increase the productivity of human recombinant factor VIII producing cell lines. The extent of increase of Factor VIII:C may be up to 2 fold, 10 fold and even 20 fold. The method is applicable to many cell lines but in particular CHO (Chinese Hamster Ovary) cells producing a full length factor VIII, deletion variants or otherwise modified factor VIII.

This invention shows that under the claimed cell fusion conditions, one can obtain high producing and stable cell lines which are not classical hybrids.

DESCRIPTION OF THE PREFERRED EMBODIMENT

Materials and Methods

Recombinant factor VIII was produced in CHO DG44 NY cells transfected with a cDNA encoding for a deletion variant of human factor VIII called factor VIII SQ.(r-VIII SQ) (see WO 91/09122 and WO 92/16557). The following cell fusion protocol was used: The cells are cultured in a proprietary serum free medium. 20–80×10$^6$ cells were washed, pelleted and a 50% (in medium) solution of PEG 4.000 was added dropwise to the pellet. After 1 minute the PEG-cell mixture was gently diluted by adding culture medium. The diluted mixture was gently centrifuged, new medium added and further cultivated in serum free medium. No selective medium was used and only one type of cell was used.

Fusion of the cells were monitored by chromosome counting and flow cytometry.

For measurement of factor VIII:C activity the growth medium was exchanged to a production medium and VIII:C measured as it accumulated in the supernatant (without medium changes) for the number of days indicated in the tables. Factor VIII activity (VIII:C) is measured by the chromogenic substrate (Chromogenix Mölndal) after various time points.

EXAMPLE 1

This example (Table 1) illustrates the r-VIII SQ expression one week after fusion. The original r-VIII SQ producing cell line "ADLA" was treated with PEG 4000 under standard fusion conditions, as described above under Materials and Methods, (ADLA PFT and PEG 1–5 in Table 1) and also when keeping the cells adhered to the plastic under subconfluency in order to prevent them from fusing (ADLA PT in Table 1). ADLA control had no PEG treatment. Cells were grown to confluence and tested for factor VIII:C.

TABLE 1

Expression of PEG treated cells compared to control cells (ADLA).

|  | Day 1 | Day 2 | Day 3 | Day 4 |
|---|---|---|---|---|
| ADLA Control | 100% | 100% | 100% | 100% |
| ADLA PT | 340% | 104% | 123% | 90% |
| ADLA PFT | 1880% | 273% | 268% | 184% |
| PEG 1 | 173% | 97% | 92% | not tested |
| PEG 2 | 236% | 138% | 152% | not tested |
| PEG 3 | 134% | 129% | 147% | not tested |
| PEG 4 | 200% | 120% | 159% | not tested |
| PEG 5 | 91% | 85% | 98% | not tested |
| Mean for fused | 457% | 140% | 153% | not tested |

Results

Cells treated under "standard" fusion conditions expressed as a mean 457%, 140% and 153% of control values day one to three after the fusion treatment. Cells PEG-treated under subconfluent conditions did only express an enhanced VIII:C activity (ADLA PT) day one after treatment. The table also shows that there are considerable differences between individual experiments and that expression is highest immediately, day one, after fusion.

EXAMPLE 2

To test the stability of the not selected, PEG-treated population one of the above cell lines (PEG 4) was further subcultured without any selective pressure for a period of 2 month and was then re-evaluated for factor VIII activity. These cells still expressed a higher amount of rVIII SQ.

TABLE 2

Stability of increased expression capability of PEG treated cells. VIII:C expression compared to control after 60 days in culture.

|  | Day 61 | Day 62 | Day 63 | Day 64 | Day 65 | Day 66 | Day 67 | Day 68 |
|---|---|---|---|---|---|---|---|---|
| Control | 100% | 100% | 100% | 100% | 100% | nt. | nt | 100% |
| PEG 4 | 100% | 907% | 1892% | 1541% | 1187% | nt | nt | 294% |

Result

The expression from day 62 to 68 after fusion, kept under nonselective conditions was between 294% and 1892% of the control values.

EXAMPLE 3

The already PEG fused cell line (PEG 4) was again PEG fused with itself, and further subcultured for 10 days without any selective pressure.

TABLE 3

VIII:C expression after retreating PEG treated cells (PEG 4) with PEG compared to non treated control cells.

|  | Day 1 | Day 2 | Day 3 | Day 4 | Day 5 | Day 6 | Day 7 |
|---|---|---|---|---|---|---|---|
| Control | 100% | 100% | 100% | 100% | 100% | 100% | 100% |
| PEG × 2 | 100% | 1933% | 1884% | 1799% | nt | nt | 490% |

Result

The twice "fusion treated cells" expressed even higher levels of r-VIII SQ compared to the single fused cells. Thus PEG treatment can be performed repeatedly.

EXAMPLE 4

The cell line PFT was further examined by chromosome counting and DNA content by fluorescence after propidium iodide staining. Table 4 shows the results of chromosome analysis after 10–20 days in culture after fusion on two different occasions. At these timepoints an increased expression as described above was present. All cell lines show a modal chromosome number of 20. All examined cells showed the presence of aberrant metaphase plates with subtetraploid chromosome numbers. There was however no differences comparing the fused cells to the control cell line. This was further studied by propidiumidodine staining and analysis of DNA content fluorescence analysis on several occasions during the propagation of the cells.

TABLE 4

Chromosome analysis. No of metaphases with the indicated chromosome number in the PEG treated cells and in the control

| Chrom numb | 18 | 19 | 20 | 21 | 22 | 24 | 32 | 34 | 36 | 37 | 38 | 39 |
|---|---|---|---|---|---|---|---|---|---|---|---|---|
| Control |  | 6 | 8 | 4 |  |  |  |  |  | 1 | 1 |  |
| ADLA PFT 1 | 2 | 2 | 7 | 3 | 1 |  |  | 2 | 1 |  |  | 1 |
| ADLA PFT 2 | 1 | 3 | 11 | 2 |  | 1 | 1 | 1 |  |  |  |  |

Result

The PEG treated cells did not have a higher DNA content compared to the non-fused control cell lines. These analysis, together with the fact that the high expression levels were stable after long time non-selective cell culture indicate that the high producer cells were not the result of a classical cell fusion process.

Discussion

Cell fusion is a well-known process. The examples presented here are though not typical for classical cell fusion. Firstly, the PEG treated cells contained neither more DNA nor chromosomes and secondly, there were no selective steps involved in subculturing the population. Furthermore the regular fusion frequencies of $10^{-4}$–$10^{-5}$ are to low for cell fusion as explanation of the long term persistence of the increased productivity. Taken together these results indicate that cell fusion with PEG treatment induce a stable change in the expression capability of the cells. As such this method is applicable to different cells and different agents.

We claim:

1. A method of obtaining a higher product expression in a producing cell line comprising fusing cells of the same origin with a fusion agent to form fused cells which produce a product.

2. A method according to claim 1, wherein the fusion agent is polyethylene glycol (PEG).

3. A method according to claim 2, in which the cells are Chinese Hamster Ovarian (CHO) cells or Chinese Hamster Ovarian (CHO) derived cell lines.

4. A method according to claim 2, in which the cells are mammalian cells or cell lines.

5. A method according to claim 2, in which the product is a therapeutically active protein or molecule.

6. A method according to claim 2 wherein the cells are selected from the group consisting of Baby Hamster Kidney (BHK) cells, BHK cell lines, Cos cells and Cos cell lines.

7. A method according to claim 1 wherein the fusion agent is selected from the group consisting of electrofusion, protoplasts and Sendaivirus.

8. A method according to claim 7, in which the cells are Chinese Hamster Ovarian (CHO) cells or Chinese Hamster Ovarian (CHO) derived cell lines.

9. A method according to claim 7, in which the cells are mammalian cells or cell lines.

10. A method according to claim 7, in which the product is a therapeutically active protein or molecule.

11. A method according to claim 7 wherein the cells are selected from the group consisting of Baby Hamster Kidney (BHK) cells, BHK cell lines, Cos cells and Cos cell lines.

12. A method according to claim 1, in which the cells are Chinese Hamster Ovary (CHO) cells or Chinese Hamster Ovarian (CHO) derived cell lines.

13. A method according to claim 12, in which the product is a therapeutically active protein or molecule.

14. A method according to claim 1, in which the cells are mammalian cells or cell lines.

15. A method according to claim 1, in which the product is a therapeutically active protein or molecule.

16. A method according to claim 15, in which the product is full length factor VIII, or rVIII SQ.

17. A method according to claim 1, in which the producing cell lines have a chromosome and DNA content identical to the original cell line.

18. A method according to claim 1, in which the fusing of the cells is performed without the presence of a selection protocol.

19. A method according to claim 1, in which a selection protocol is used.

20. A method according to claim 1, in which the fusing of the cells is performed on already fused cells.

21. A method according to claim 1 wherein the cells are selected from the group consisting of Baby Hamster Kidney (BHK) cells, BHK cell lines, Cos cells and Cos cell lines.

* * * * *